United States Patent
Oishi

(10) Patent No.: US 10,548,541 B2
(45) Date of Patent: Feb. 4, 2020

(54) MEDICAL IMAGE DIAGNOSIS APPARATUS AND BED APPARATUS

(71) Applicant: Toshiba Medical Systems Corporation, Otawara-shi (JP)

(72) Inventor: Keisuke Oishi, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 320 days.

(21) Appl. No.: 15/704,452

(22) Filed: Sep. 14, 2017

(65) Prior Publication Data

US 2018/0078223 A1    Mar. 22, 2018

(30) Foreign Application Priority Data

Sep. 16, 2016  (JP) ................................ 2016-181665

(51) Int. Cl.
    A61B 6/04  (2006.01)
    A61B 6/03  (2006.01)
    A61B 6/00  (2006.01)

(52) U.S. Cl.
    CPC ............ *A61B 6/0407* (2013.01); *A61B 6/032* (2013.01); *A61B 6/0457* (2013.01); *A61B 6/5205* (2013.01)

(58) Field of Classification Search
    CPC ..... A61B 6/0407; A61B 6/0457; A61B 6/032; A61B 6/5205; A61B 6/461
    See application file for complete search history.

(56) References Cited

U.S. PATENT DOCUMENTS

| 4,613,122 A | 9/1986 | Manabe | |
| 9,113,804 B2* | 8/2015 | Kimishima | A61B 6/0407 |
| 2006/0104422 A1* | 5/2006 | Iisaku | A61B 6/04 378/209 |
| 2017/0095219 A1* | 4/2017 | Wakahara | A61B 6/0407 |
| 2017/0303873 A1* | 10/2017 | Toya | A61B 6/0407 |
| 2018/0078223 A1* | 3/2018 | Oishi | A61B 6/0407 |
| 2018/0177479 A1* | 6/2018 | Sato | A61B 6/0407 |
| 2019/0000404 A1* | 1/2019 | Osaki | A61B 6/0457 |
| 2019/0105010 A1* | 4/2019 | Oishi | A61B 6/548 |

FOREIGN PATENT DOCUMENTS

| JP | 60-041955 | 3/1985 |
| JP | 08-322829 | 12/1996 |
| JP | 2006-061194 | 3/2006 |
| JP | 2006-141577 | 6/2006 |
| WO | 2010/123024 | 10/2010 |

* cited by examiner

*Primary Examiner* — Michael C Bryant
(74) *Attorney, Agent, or Firm* — Oblon, McClelland, Maier & Neustadt, L.L.P.

(57) ABSTRACT

According to one embodiment, a medical image diagnosis apparatus includes a gantry, a first frame, a second frame, a support base, and control circuitry. The first frame supports a table top. The table top is movable in a longitudinal direction of the table top. The second frame supports the first frame. The first frame is movable in the longitudinal direction. The support base is equipped with an X link that supports the second frame. The second frame is movable in a direction vertical to a floor surface. The control circuitry moves the first frame in the longitudinal direction based on operation information of a drive shaft of the support base to correct a change in position of the first frame in the longitudinal direction in accordance with movement of the second frame in the vertical direction.

10 Claims, 11 Drawing Sheets

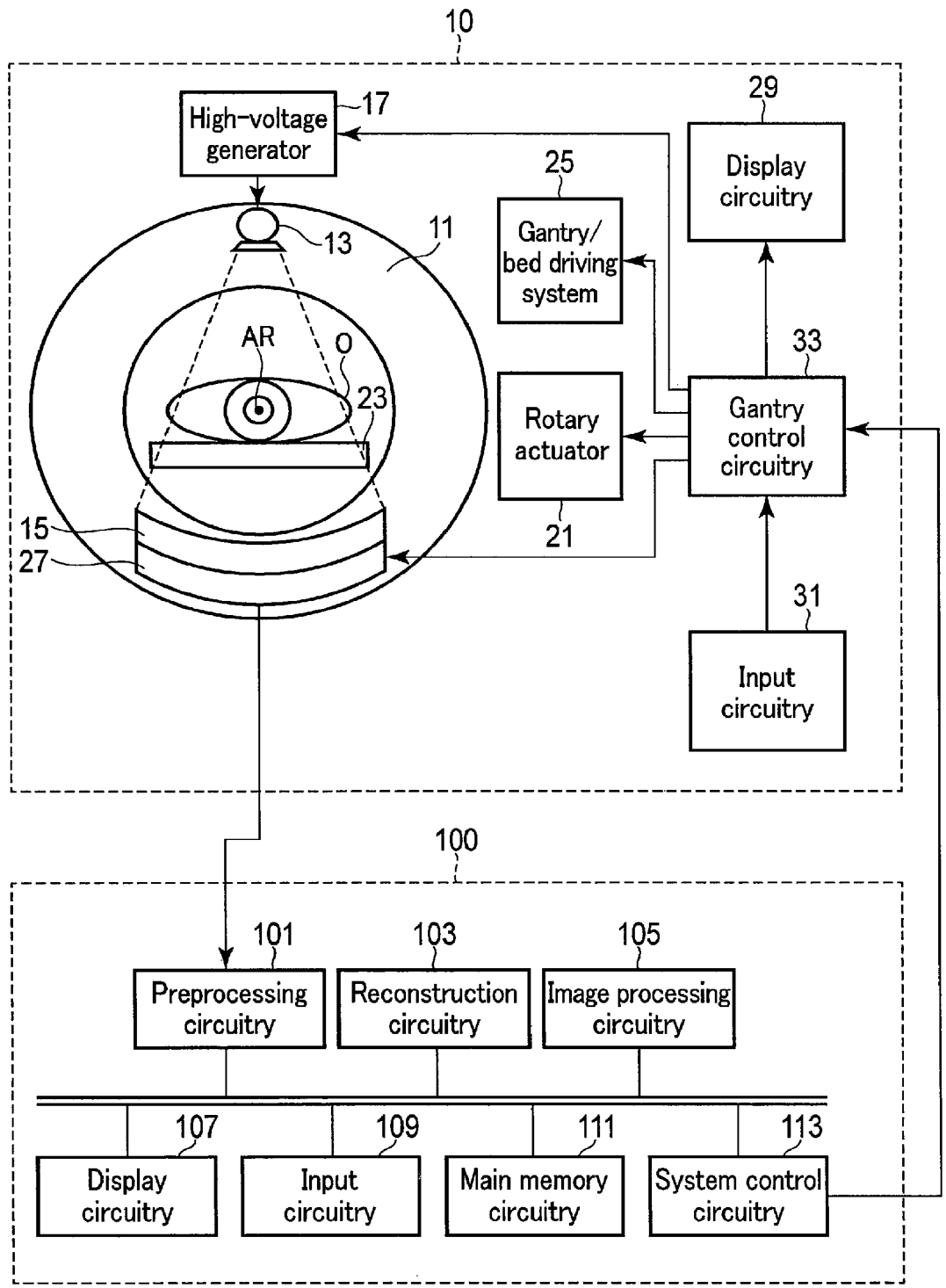
F I G. 1

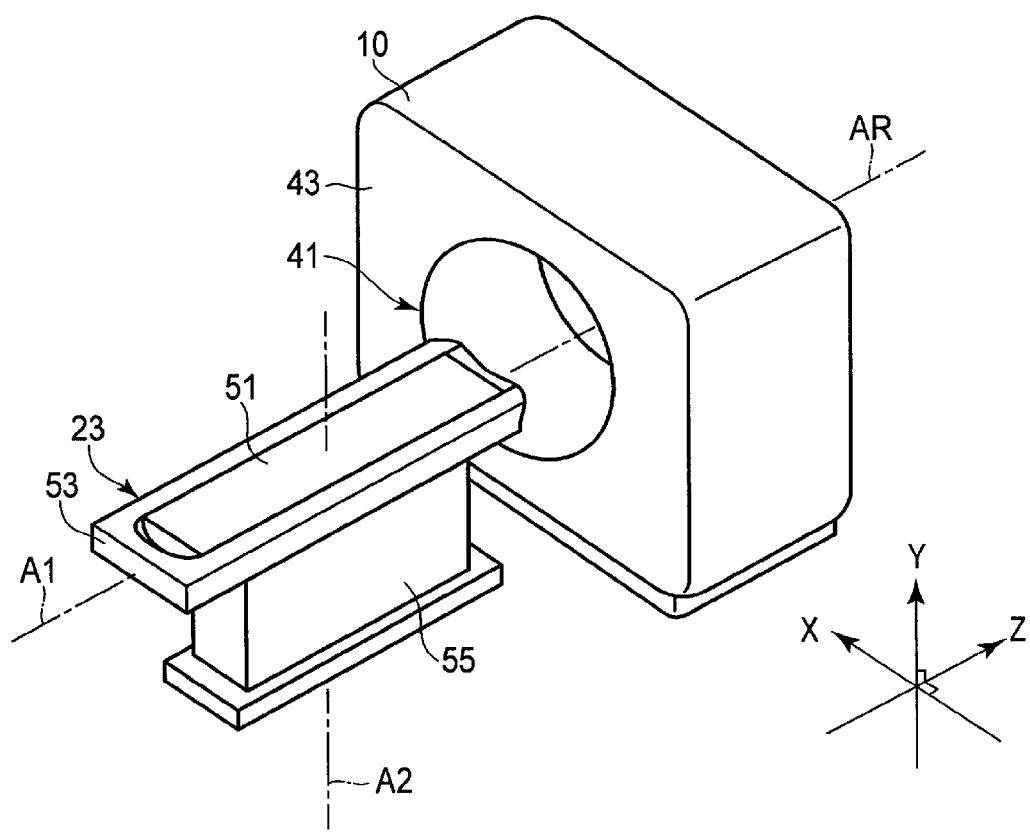
F I G. 2

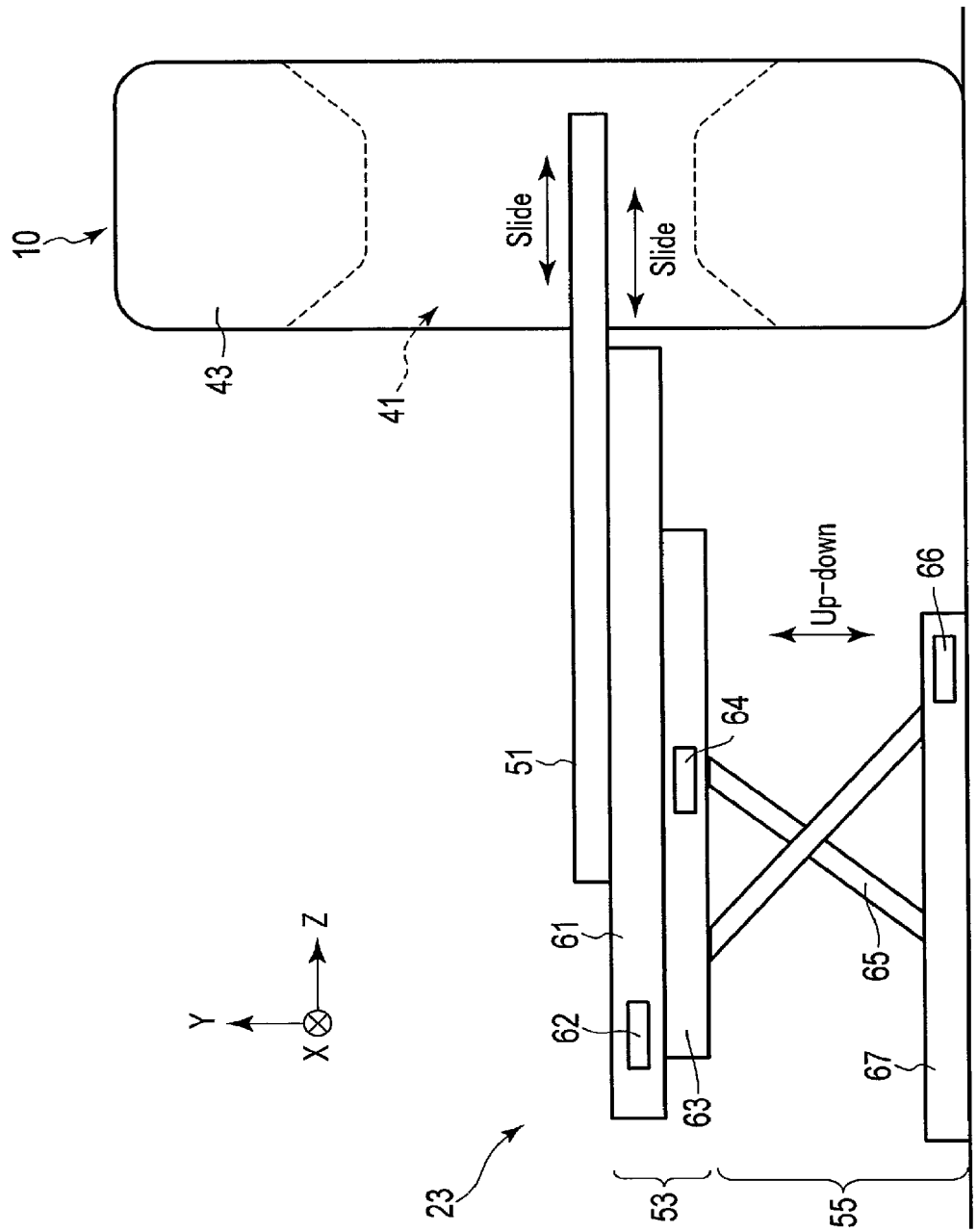
F I G. 3

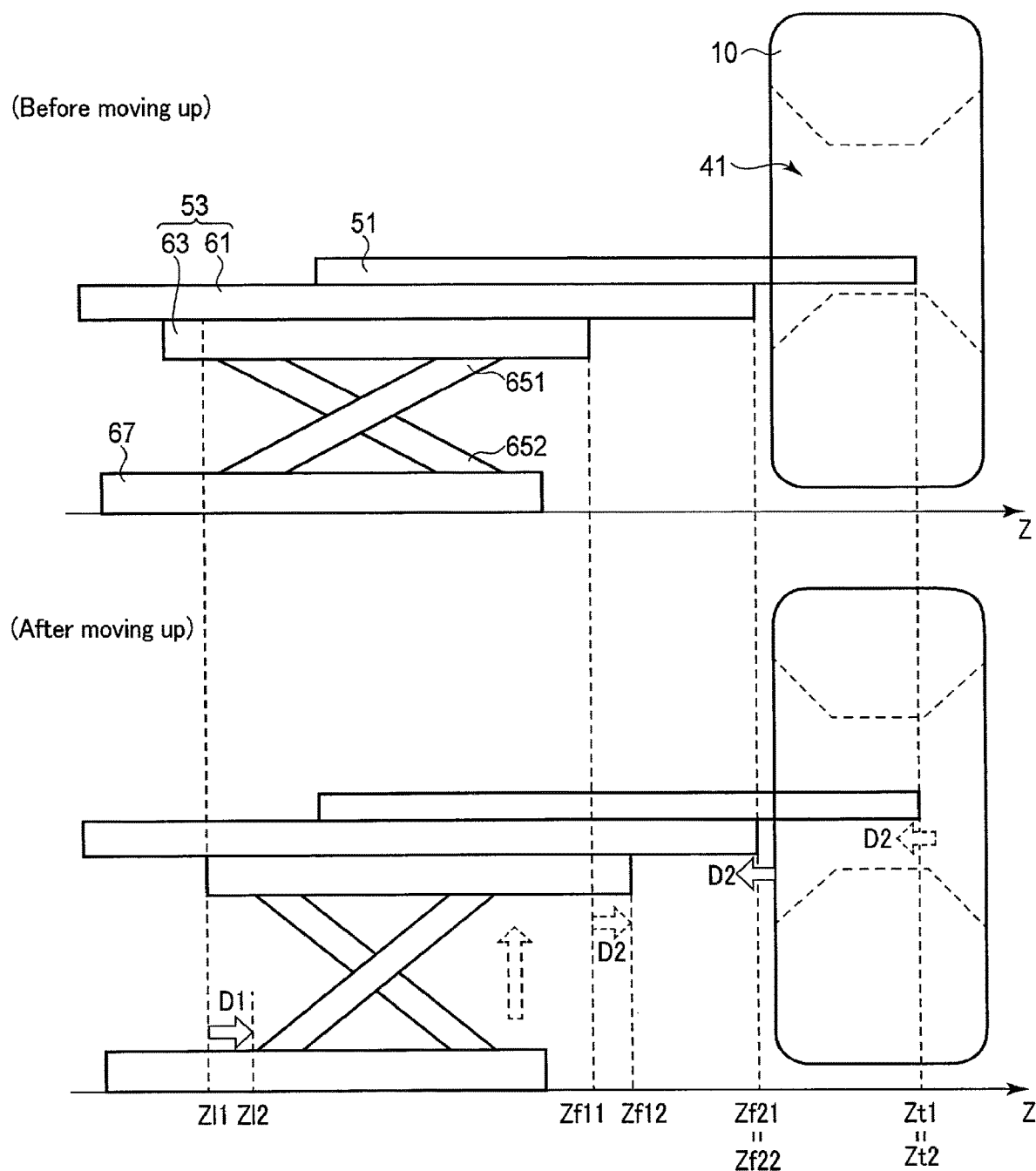
F I G. 8

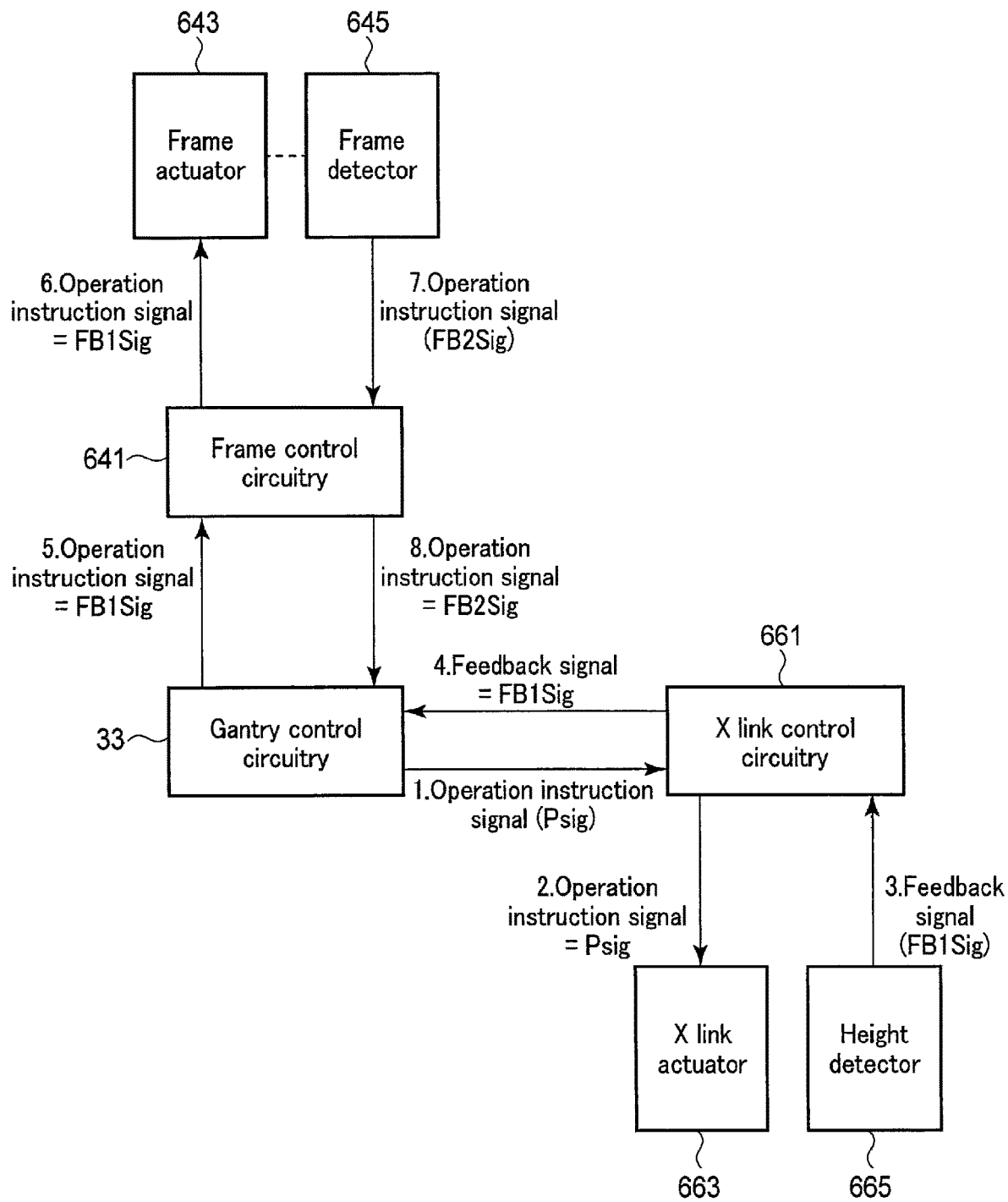
F I G. 9

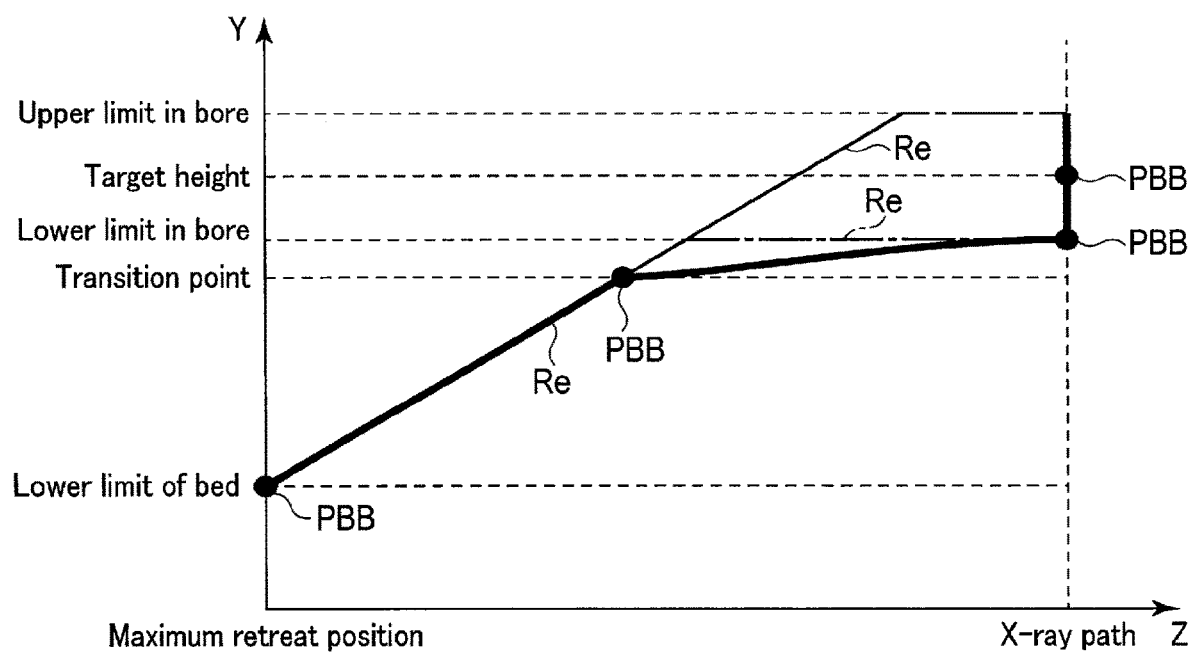
F. I G. 11

MEDICAL IMAGE DIAGNOSIS APPARATUS AND BED APPARATUS

CROSS-REFERENCE TO RELATED APPLICATIONS

This application is based upon and claims the benefit of priority from the prior Japanese Patent Application No. 2016-181665, filed Sep. 16, 2016 the entire contents of which are incorporated herein by reference.

FIELD

Embodiments described herein relate generally to a medical image diagnosis apparatus and a bed apparatus.

BACKGROUND

To obtain a high-definition image, reduction in bending or vibration of a table top in a bore is required. For this purpose, a bed apparatus, in which a support frame supporting the table top can approach to a gantry, has been developed. For example, in a known system, the table top and the support frame move forward and backward while moving up and down. If this system is adopted, when the table top and the support frame are moved up, they inevitably protrude. To avoid this protrusion during positioning of the table top and the support frame in a bore, the position in a forward-backward direction of the table top and the support frame is corrected based on the position in an up-down direction thereof. However, this system cannot correct the position accurately, because movement information on directions other than the forward-backward direction, for example, the up-down direction, need to be converted to a position in the forward-backward direction.

BRIEF DESCRIPTION OF THE DRAWINGS

FIG. 1 is a view showing a configuration of an X-ray computed tomography apparatus according to the present embodiment.

FIG. 2 is a schematic view showing an appearance of a gantry and a bed according to the present embodiment.

FIG. 3 is a schematic view showing a side of the bed according to the present embodiment.

FIG. 8 is a diagram showing a positional relationship between the bed and the gantry before moving up and after moving up, involving protrusion correction according to the present embodiment.

FIG. 9 is a schematic diagram showing flows of operation instruction signals among the gantry control circuitry, an X link actuation controller, and a frame actuation controller in a protrusion correction operation according to the present embodiment.

FIG. 11 is a diagram showing a movement path of the table top in the example of the operation shown in FIG. 10.

DETAILED DESCRIPTION

Figure 4:
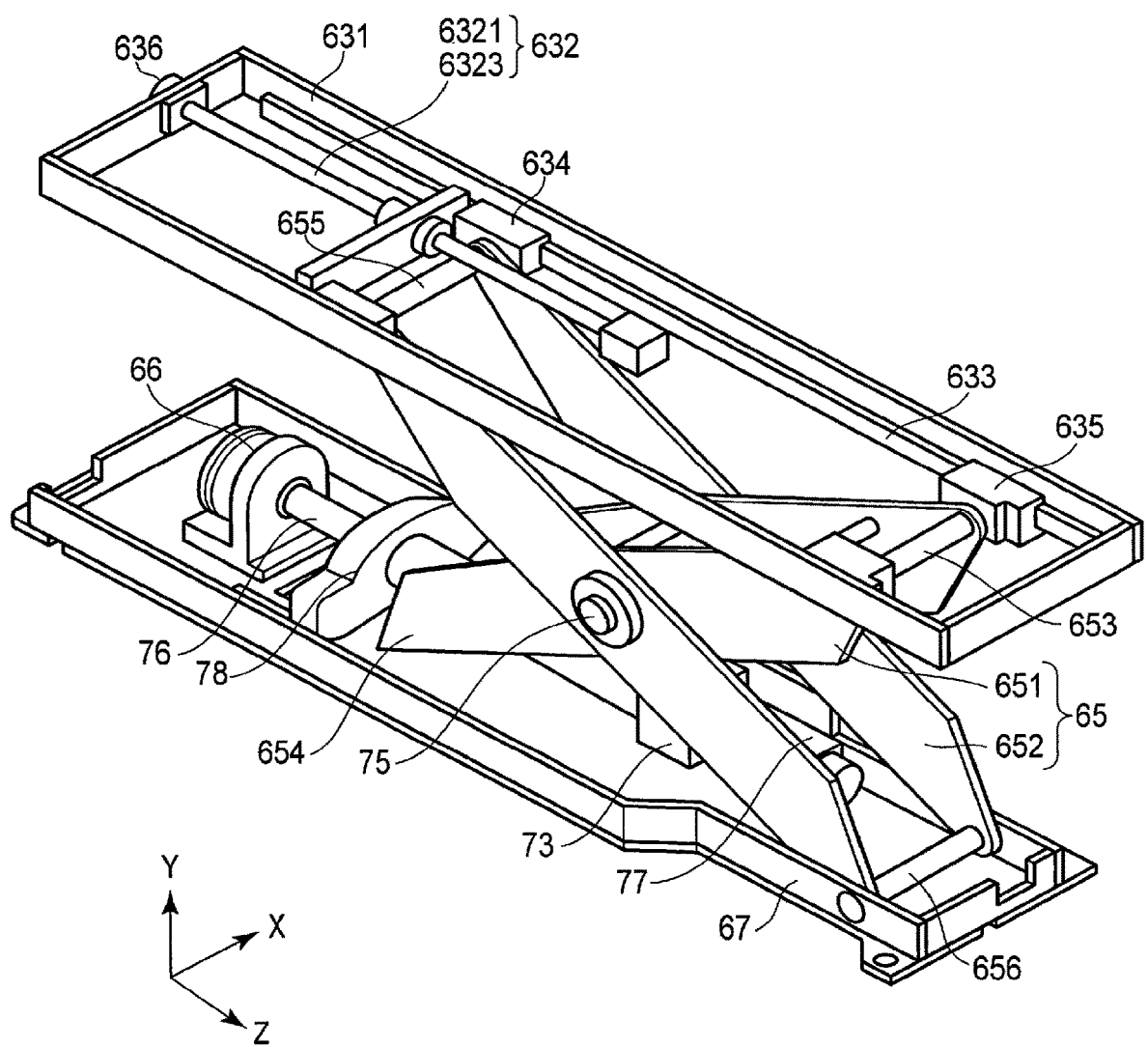
FIG. 4 is a perspective view of a lower frame, an X link, and a base of the bed according to the present embodiment.

A medical image diagnosis apparatus according to the present embodiment includes a gantry, a first frame, a second frame, a support base, and movement control circuitry. The first frame supports a table top on which a subject is laid, so that the table top is movable in a longitudinal direction of the table top that moves toward the gantry. The second frame supports the first frame, so that the first frame is movable in the longitudinal direction. The support base is equipped with an X link that supports the second frame, so that the second frame is movable in a direction vertical to a floor surface. The movement control circuitry moves the first frame in the longitudinal direction based on operation information of a drive shaft of the support base to correct a change in position of the first frame in the longitudinal direction in accordance with movement of the second frame in the vertical direction.

The medical image diagnosis apparatus and a bed apparatus according to the present embodiment will be explained with reference to the accompanying drawings.

The bed apparatus of the present embodiment is a medical imaging bed apparatus for use in a medical image diagnosis apparatus, such as an X-ray computed tomography apparatus, an X-ray diagnosis apparatus, a PET (Positron Emission Tomography) apparatus, and a SPECT (Single Photon Emission Computed Tomography). The bed apparatus of the present embodiment is not limited to a single-modality apparatus as mentioned above, but may be used in a multimodality apparatus, such as a PET/CT apparatus, a SPECT/CT apparatus, or an IVR (InterVentional Radiology)/CT apparatus. In the following, the bed apparatus of the present embodiment is assumed to be mounted in an X-ray computed tomography apparatus.

FIG. 1 shows a configuration of an X-ray computed tomography apparatus according to the present embodiment. As shown in FIG. 1, the X-ray computed tomography apparatus of the present embodiment includes a gantry 10 and a console 100. For example, the gantry 10 is placed in a CT examination room, and the console 100 is placed in a control room adjacent to the CT examination room. The gantry 10 and the console 100 are communicatably connected to each other. The gantry 10 is mounted with a scan mechanism to carry out an X-ray CT scanning of a subject O. The console 100 is a computer that controls the gantry 10.

As shown in FIG. 1, the gantry 10 includes a rotating frame 11 of an approximately cylindrical shape, in which a bore serving as a field of view is formed. As shown in FIG. 1, an X-ray tube 13 and an X-ray detector 15 are attached to the rotating frame 11 on opposite sides of the bore. The rotating frame 11 is a metal frame having an annular shape made of metal, such as aluminum. As will be detailed later, the gantry 10 includes a main frame formed of metal, such as aluminum. The rotating frame 11 is supported by the main frame via a bearing or the like so as to be rotatable around a central axis AR. A slip ring (not shown) is provided in a contact portion between the main frame and the rotating frame 11. A conductive brush (not shown) is attached to the contact portion to be slidably brought into contact with the slip ring. Electric power from a power supply (not shown) housed in the gantry 10 is supplied via the slip ring and the brush to various devices, such as the X-ray detector 15 and a high-voltage generator 17, mounted on the rotating frame 11.

The X-ray tube 13 is connected to the high-voltage generator 17. The high-voltage generator 17 is attached to, for example, the rotating frame 11. The high-voltage generator 17 generates, from the electric power supplied via the slip ring and the brush from the power supply (not shown) in the gantry, a high voltage to be applied to the X-ray tube 13 and supplies a filament heating current under the control of gantry control circuitry 33. The high-voltage generator 17 and the X-ray tube 13 are connected through a high-voltage cable (not shown). The high voltage generated by the high-voltage generator 17 is applied to the X-ray tube 13 through the high-voltage cable. Furthermore, the filament heating current generated by the high-voltage generator 17 is applied to the X-ray tube 13 through the high-voltage cable.

The rotating frame 11 rotates at a constant angular speed about the central axis AR upon receipt of motive power from a rotary actuator 21 A discretionarily selectable motor, such as a direct drive motor or a servo motor, may be used as the rotary actuator 21. The rotary actuator 21 is housed in, for example, the gantry 10. The rotary actuator 21 generates motive power to rotate the rotating frame 11 upon receipt of a drive signal from the gantry control circuitry 33.

An FOV (Field of View) is set in the bore of the rotating frame 11. The table top supported by the bed 23 is inserted into the bore of the rotating frame 11. The subject O is laid on the table top. The bed 23 is, for example, a two-stage slide type. The bed 23 freely moves the table top upon receipt of motive power from a gantry/bed driving system 25. Details of the bed 23 and the gantry/bed driving system 25 will be described later. The table top is positioned so that the FOV includes a part to be imaged of the subject O laid on the table top.

The gantry/bed driving system 25 includes an actuation controller relating to a movement of the gantry 10, such as a tilt and a slew of the gantry 10, and an actuation controller relating to a movement of the bed 23. The gantry/bed driving system 25 generates motive power upon receipt of a drive signal from the gantry control circuitry 33. Details of the gantry/bed driving system 25 will be described later.

The X-ray detector 15 detects an X-ray generated by the X-ray tube 13. Specifically, the X-ray detector 15 includes a plurality of detector elements arranged on a two-dimensional curved face. Each of the detector elements includes a scintillator and a photoelectric conversion element. The scintillator is formed of a material that converts an X ray to fluorescence. The scintillator converts an input X ray to fluorescent photons of the number corresponding to an intensity of the input X ray. The photoelectric conversion element is a circuit element that amplifies and converts fluorescence to an electric signal. For example, a photomultiplier tube or a photodiode is used as the photoelectric conversion element. The detector element may be of an indirect conversion type that converts an X-ray into fluorescence and then an electrical signal, or a direct conversion type that converts an X-ray directly into an electrical signal. For example, a type including a semiconductor diode, which is formed by connecting two electrodes to the respective ends of a semiconductor, is applicable as the direct conversion-type detector element.

Data acquisition circuitry 27 is connected to the X-ray detector 15. The data acquisition circuitry 27 collects data corresponding to the intensity of the X ray detected by the X-ray detector 15 (hereinafter referred to as raw data) from the X-ray detector 15 for each view. Specifically, the data acquisition circuitry 27 acquires integrating circuitry (not shown) and an A/D converter (not shown) for each detector element. The integrating circuitry integrates an electric signal from the detector element for each view. The A/D converter converts the integrated electric signal of an analog signal to a digital signal (raw data). As a result, raw data for each view is acquired. The raw data is a set of digital values indicating the intensity of X-rays identified by a channel number and a row number of a detector element of the generation source, and a view number indicating the collected view. The raw data is supplied to the console 100 via a non-contact data transmitter (not shown) housed in the gantry 10. Another circuit element, such as a preamplifier or an IV converter, may be mounted on the data acquisition circuitry 27. The data acquisition circuitry 27 includes a semiconductor integrated circuit, such as ASIC (Application Specific Integrated Circuit). The circuit elements, such as the aforementioned integrating circuitry or A/D converter, are mounted on the semiconductor integrated circuit.

The display circuitry 29 displays various information, such as a geometric arrangement of the bed 23 and the gantry 10, and scan conditions. Specifically, the display circuitry 29 includes display interface circuitry and a display device. The display interface circuitry converts data representing a display target to a video signal. A display signal is supplied to the display device. The display device is provided on a surface of the gantry 10. The display device displays the video signal representing the display target. As the display device, for example, a CRT display, a liquid crystal display, an organic EL display, an LED display, a plasma display, or any other display known in this technical field may be used as appropriate.

The input circuitry 31 inputs various instructions relating to movement of the bed 23 or the gantry 10 from a user. Specifically, the input circuitry 31 includes an input device and input interface circuitry. The input device accepts various instructions from the user. As the input device, an operation panel or various switches may be used. The input interface circuitry supplies an output signal from the input device to the gantry control circuitry 33 through a bus.

The gantry control circuitry 33 synchronously controls the high-voltage generator 17, the rotary actuator 21, the gantry/bed driving system 25, and the data acquisition circuitry 27 to carry out X-ray CT scanning in accordance with scan conditions made by system control circuitry 113 of the console 100. Furthermore, the gantry control circuitry 33 controls the gantry/bed driving system 25, and moves the gantry 10 and the bed 23 in cooperation with each other to achieve positioning of the gantry 10 and the bed 23 with less bending and vibration of the table top. The gantry control circuitry 33 includes a processor, such as a CPU (Central Processing Unit) and an MPU (Micro Processing Unit), and a memory, such as a ROM (Read Only Memory) and a RAM (Random Access Memory), as hardware resources. The gantry control circuitry 33 may be implemented as an ASIC or a FPGA (Field Programmable Gate Array), a CPLD (Complex Programmable Logic Device), or an SPLD (Simple Programmable Logic Device). Details of the gantry control circuitry 33 will be described later.

As shown in FIG. 1, the console 100 includes preprocessing circuitry 101, reconstruction circuitry 103, image processing circuitry 105, display circuitry 107, input circuitry 109, main memory circuitry 111, and system control circuitry 113. Data communication among the preprocessing circuitry 101, the reconstruction circuitry 103, the image processing circuitry 105, the display circuitry 107, the input circuitry 109, the main memory circuitry 111, and the system control circuitry 113 is carried out through a bus.

The preprocessing circuitry 101 includes a processor such as a GPU (Graphics Processing Unit), and a memory, such as a ROM or a RAM, as hardware resources. The preprocessing circuitry 101 subjects the raw data transmitted from the gantry 10 to preprocessing, such as logarithmic conversion. The preprocessed raw data is referred to also as projection data.

The reconstruction circuitry 103 includes a processor, such as a CPU, an MPU, or a GPU, and a memory, such as a ROM or a RAM, as hardware resources. The reconstruction circuitry 103 generates a CT image representing a space distribution of CT values relating to the subject O based on the raw data after the preprocessing. The image reconstruction may be carried out by a known image reconstruction algorithm, for example, an analytical image reconstruction method, such as an FBP (Filtered Back Projection) method or a CBP (Convolution Back Projection) method, or a statistical image reconstruction method, such as an ML-EM (Maximum Likelihood Expectation Maximization) method or an OS-EM (Ordered Subset Expectation Maximization) method.

The image processing circuitry 105 performs various types of image processing for a CT image reconstructed by the reconstruction circuitry 103. For example, the image processing circuitry 105 performs three-dimensional image processing, such as volume rendering, surface volume rendering, pixel value projection processing, MPR (Multi-Planer Reconstruction) processing, or CPR (Curved MPR) processing, to generate a display image. The image processing circuitry 105 includes a processor, such as a CPU, an MPU, or a GPU, and a memory, such as a ROM or a RAM, as hardware resources. The image processing circuitry 105 may be implemented as an ASIC, an FPGA, a CPLD, or an SPLD.

The display circuitry 107 displays various data, such as a two-dimensional CT image and a display image. Specifically, the display circuitry 107 includes a display interface and a display device. The display interface converts data representing a display target to a video signal. A display signal is supplied to the display device. The display device displays the video signal representing the display target. As the display device, for example, a CRT display, a liquid crystal display, an organic EL display, an LED display, a plasma display, or any other display known in this technical field may be used as appropriate.

The input circuitry 109 accepts various instructions from the user. Specifically, the input circuitry 109 includes an input device and an input interface. The input device accepts various instructions from the user. As the input device, a keyboard, a mouse, or switches etc. may be used. The input interface supplies an output signal from the input device to the system control circuitry 113 through a bus.

The main memory circuitry 111 is a memory which stores various information, such as an HDD, an SSD, and an integrated circuit memory. The main memory circuitry 111 may be a driver which writes and reads information to and from portable memories, such as a CD-ROM drive, a DVD drive, and a flash memory. The main memory circuitry 111 stores data of, for example, a CT image and a display image. Furthermore, the main memory circuitry 111 stores a control program and the like relating to X-ray CT scanning according to the embodiment.

The system control circuitry 113 includes a processor, such as a CPU or an MPU, and a memory, such as a ROM or a RAM, as hardware resources. The system control circuitry 113 may be implemented as an ASIC, an FPGA, a CPLD, or an SPLD. The system control circuitry 113 functions as a center of the X-ray computed tomography apparatus according to the present embodiment. Specifically, the system control circuitry 113 reads the control program stored in the main memory circuitry 111 and expands it in the memory, and controls the sections of the X-ray computed tomography apparatus in accordance with the expanded control program.

The functions of the preprocessing circuitry 101, the reconstruction circuitry 103, the image processing circuitry 105, and the system control circuitry 113 may be implemented by a single processor, or a plurality of programs.

A positional relationship between the gantry 10 and the bed 23 according to the present embodiment will be explained with reference to FIG. 2. FIG. 2 is a schematic view showing an appearance of the gantry 10 and the bed 23 according to the embodiment. As shown in FIG. 2, the gantry 10 includes a housing 43 in which a nearly cylindrical bore 41 is formed. The housing 43 houses the rotating frame 11, to which the X-ray tube 13 and the X-ray detector 15 are attached on opposite sides of the bore 41.

The bed 23 is set in front of the gantry 10. The bed 23 is equipped with the table top 51, the support frame 53, and the support base 55. The table top 51 is disposed so that a longitudinal axis A1 of the table top 51 is parallel to the central axis AR of the bore 41. The support frame 53 supports the table top 51 so that the table top 51 is slidable along the longitudinal axis A1. The support base 55 supports the support frame 53 so that the support frame 53 is slidable along an axis parallel to the longitudinal axis A1 and movable up and down along a vertical axis A2 vertically perpendicular to the longitudinal axis A1. The support base 55 has an overhanging support structure. More specifically, the support base 55 supports the table top 51 and the support frame 53 at only one side with respect to the longitudinal axis A1. An axis parallel to the longitudinal axis A1 is defined as a Z axis, and an axis parallel to the vertical axis A2 is defined as a Y axis. An axis perpendicular to the Z axis and the Y axis is defined as an X axis. The XYZ coordinate system forms an orthogonal coordinate system. A direction parallel to the longitudinal axis A1 of the table top 51 is referred to as a longitudinal direction, a forward-backward direction, or a Z direction. A direction parallel to the vertical axis A2 is referred to as an up-down direction or a Y direction. A direction in which the bed 23 moves closer to the gantry 10 is referred to as a forward direction or a +Z direction, a direction in which the bed 23 moves away from the gantry 10 is referred to as a backward direction or a −Z direction, a direction in which the bed 23 moves up from the floor is referred to as an upward direction or a +Y direction, and a direction in which the bed 23 moves down toward the floor is referred to as a downward direction or a −Y direction.

Next, a structure of the bed 23 will be described. FIG. 3 is a schematic view showing a side of the bed 23 according to the present embodiment. In FIG. 3, a housing of the bed 23 is not shown. As shown in FIG. 3, the bed 23 is set in front of the gantry 10 (the −Z direction). As shown in FIG. 3, the bed 23 includes the table top 51, the support frame 53, and the support base 55. A subject O is laid on the table top 51. The table top 51 is a flexible plate-like structure. The table top 51 is made of a material having a relatively-high X-ray transmittance, for example, urethane foam or carbon.

The table top 51 is supported by the support frame 53 so as to be slidable in the Z direction. The support frame 53 includes an upper frame 61 and a lower frame 63. The upper frame 61 supports the table top 51 from the bottom. The upper frame 61 may have any structure as long as it can slidably support the table top 51. For example, the upper frame 61 includes a robust frame (not shown) that supports the table top 51, and a guide rail (not shown) that guides the table top 51 in the Z direction. The upper frame 61 is provided with an actuation controller (hereinafter referred to as a table top actuation controller) 62 to slide the table top 51. The table top actuation controller 62 actuates the upper frame 61 to slide the table top 51 upon receipt of an operation instruction from the gantry control circuitry 33.

The lower frame 63 supports the upper frame 61 from the bottom. The lower frame 63 supports the upper frame 61 so that the upper frame 61 is slidable in the Z direction. The lower frame 63 may have any structure as long as it can slidably support the upper frame 61. The lower frame 63 is implemented by, for example, a ball screw. The lower frame 63 is provided with an actuation controller 64 to slide the upper frame 61 (hereinafter referred to as a frame actuation controller). The frame actuation controller 64 actuates the lower frame 63 to slide the upper frame 61 upon receipt of an operation instruction from the gantry control circuitry 33.

The support base 55 is disposed on the floor surface. The support base 55 has a supporting structure that allows the lower frame 63 to move closer (forward) to or away (backward) from the gantry 10, while moving up or down in the Y direction. The support base 55 includes, for example, an X link 65, and a base 67. The X link 65 is connected to the lower frame 63 and the base 67. The base 67 is provided with an actuation controller (hereinafter referred to as an X link actuation controller) 66 to move the lower frame 63 up and down by the X link 65. The X link actuation controller 66 actuates the X link 65 to move the lower frame 63 up and down upon receipt of an operation instruction from the gantry control circuitry 33.

FIG. 4 is a perspective view showing the lower frame 63, the X link 65, and the base 67. As shown in FIG. 4, the lower frame 63 includes a support frame 631. The support frame 631 is a metal frame having a rectangular shape and extending in the Z direction. The support frame 631 is provided with a ball screw 632. The ball screw 632 includes a threaded shaft 6321 and a slider 6323. The ball screw 632 is provided in the support frame 631 to extend in the Z direction. The upper frame 61 (not shown in FIG. 4) is attached to the slider 6323 of the ball screw 632. Guide rails 633 to guide the slide of the ball screw 632 in the Z direction are provided on the support frame 631. An end 636 of the ball screw 632 is provided on the support frame 631 so as to be rotatable around the shaft center. The threaded shaft 6321 of the ball screw 632 moves in cooperation with a rotation of a drive shaft of the frame actuation controller 64. The slider 6323 of the ball screw 632 slides along the shaft center of the threaded shaft 6321. Preferably, the ball screw 632 may be provided with a stopper that mechanically limits a movable range of the ball screw 632.

In the above description, the support frame 631 is described as rectangular. However, the embodiment is not limited to the description. For example, the support frame 631 may be a pair of beam-like frames to which the guide rails 633 are attached. In this case, the support frame 631 does not need a pair of frames in a short axis direction (X axis direction).

The X link 65 includes a pair of links (a movable link 651 and a fixed link 652), which are pivotally supported to form an X shape. The movable link 651 and the fixed link 652 are rotatable around a fulcrum 75. Each of the movable link 651 and the fixed link 652 is formed of a pair of metal plates that are almost the same in length. One end 656 of the fixed link 652 on the side of the base 67 is fixed to the base 67. The end 656 is preferably fixed with, for example, a fastener. Another end 655 of the fixed link 652 is fixed to the support frame 631. More specifically, the end 655 is fixed to rollers 634 provided on a pair of frames on the long sides of the support frame 631. The rollers 634 are fixed to the guide rails 633 with a fastener or the like. As a result, the end 655 can be fixed to the support frame 631.

One end 654 of the movable link 651 on the side of the base 67 is supported by the base 67 so as to be slidable in the Z direction. Specifically, a lead screw 76 is inserted through the end 654. One end of the lead screw 76 is connected to the X link actuation controller 66. The X link actuation controller 66 is disposed on the base 67. A brake 77 is attached to another end of the lead screw 76. A nut 78 is attached to the lead screw 76 between the end 654 and the X link actuation controller 66. The nut 78 is a structural element having a through hole with a thread groove that is screwed to threads of the lead screw 76. Another end 653 of the movable link 651 is supported by the support frame 631 so as to be slidable in the Z direction. Specifically, the other end 653 is fixed to rollers 635 provided on a pair of frames on the long sides of the support frame 631. The rollers 635 are fixed to the guide rails 633 so as to be slidable in the Z direction. In other words, the guide rails 633 provided on the support frame 631 guide both a slide of the slider 6323 (that is, the upper frame 61) in the Z direction and a slide of the movable link 651 in the Z direction with the same rails.

The lead screw 76 rotates around the shaft center in cooperation with a rotation of the X link actuation controller 66 around a drive shaft. The nut 78 slides along the shaft center of the lead screw 76, that is, in the Z direction, in cooperation with the rotation of the lead screw 76. For example, when the lead screw 76 rotates in a forward direction, the nut 78 slides in the +Z direction. When the lead screw 76 rotates in a backward direction, the nut 78 slides in the −Z direction. The sliding of the nut 78 in the +Z direction presses the movable link 651 in the +Z direction, and reduces the distance between the movable link 651 and the fixed link 652 in the Z direction. As a result, the lower frame 63 is moved up. The sliding of the nut 78 in the −Z direction releases the movable link 651 from the pressure in the +Z direction, and increases the distance between the movable link 651 and the fixed link 652 in the Z direction. As a result, the lower frame 63 is moved down.

Figure 5:
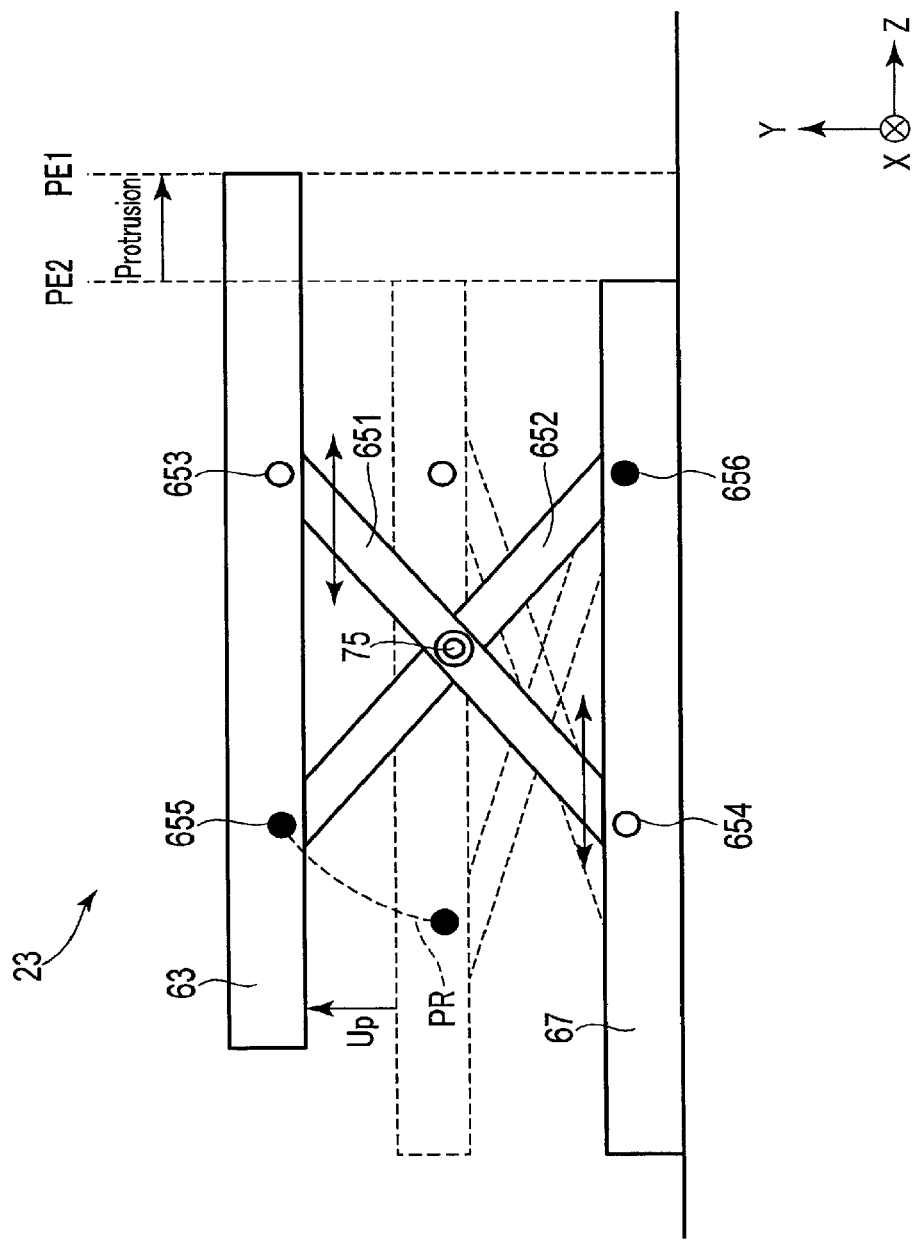
FIG. 5 is a view showing protrusion of the bed according to the present embodiment.

Next, a principle of protrusion of the bed 23 of a two-stage slide type according to the present embodiment will be explained. FIG. 5 is a view showing protrusion of the bed 23 according to the present embodiment. In FIG. 5, the bed 23 at a lower limit is indicated by dotted lines, and the bed 23 at a moved-up position is indicated by solid lines.

As shown in FIG. 5, it is assumed that an end of the lower frame 63 in the Z direction at the lower limit, more specifically, an end of the support frame 631 of the lower frame 63 in the Z direction, is located at a position PE2 in the Z direction. As described above, the end 653 of the movable link 651 is slidable in the Z direction on the lower frame 63, and the end 654 is slidable in the Z direction on the base 67. The end 655 of the fixed link 652 is fixed to the lower frame 63, and the end 656 is fixed to the base 67. Therefore, pressure of the movable link 651 by the nut 78 causes the end 655 to move along an arc PR around the end 656 as a fulcrum, and having a radius equal to the distance between the end 655 and the end 656. Before and after this movement, the position of the end 655 in the lower frame 63 and the position of the end 656 in the base 67 do not change.

Accordingly, the end of the lower frame 63 in the Z direction protrudes toward the gantry 10. For example, when the table top is moved up to a target height, the end of the lower frame 63 in the Z direction protrudes to a position PE1 that is nearer to the gantry 10 than the position PE2 at the lower limit is.

Thus, the lower frame 63 protrudes toward the gantry 10, so that the upper frame 61 supported by the lower frame 63 can be close to the gantry 10 until just before being in contact with the gantry 10. Therefore, when the table top 51 is inserted in the bore 41, the bending and vibration of the table top 51 can be reduced.

With the above structure, when the lower frame 63 is moved down, the lower frame 63 moves away from the gantry 10 as it is lowered. Specifically, if the table top 51 is moved down from the target height to the lower limit, the end of the lower frame 63 in the Z direction will be retracted from the position PE1 to the position PE2.

In the X link 65 of this embodiment, the two ends of one of the links (the fixed link 652) are fixed, whereas the two ends of the other link (the movable link 651) are floating. Accordingly, as the table top 51 and the support frame 53 are moved up and down by the X link 65, the table top 51 and the lower frame 63 inevitably move forward and backward. For example, if the table top 51 and the upper frame 61 are moved up after positioning of the table top 51 and the upper frame 61 is completed, the table top 51 and the upper frame 61 will be displaced in the Z direction as the lower frame 63 protrudes. The displaced table top 51 and upper frame 61 need to be repositioned.

The gantry control circuitry 33 of the present embodiment corrects the displacement of the upper frame 61 in the Z direction as the lower frame 63 is moved up and down by the X link 65. Displacement correction by the gantry control circuitry 33 will be explained in detail below. First, configurations of the gantry/bed driving system 25 and the gantry control circuitry 33 of the embodiment will be explained.

Figure 6:
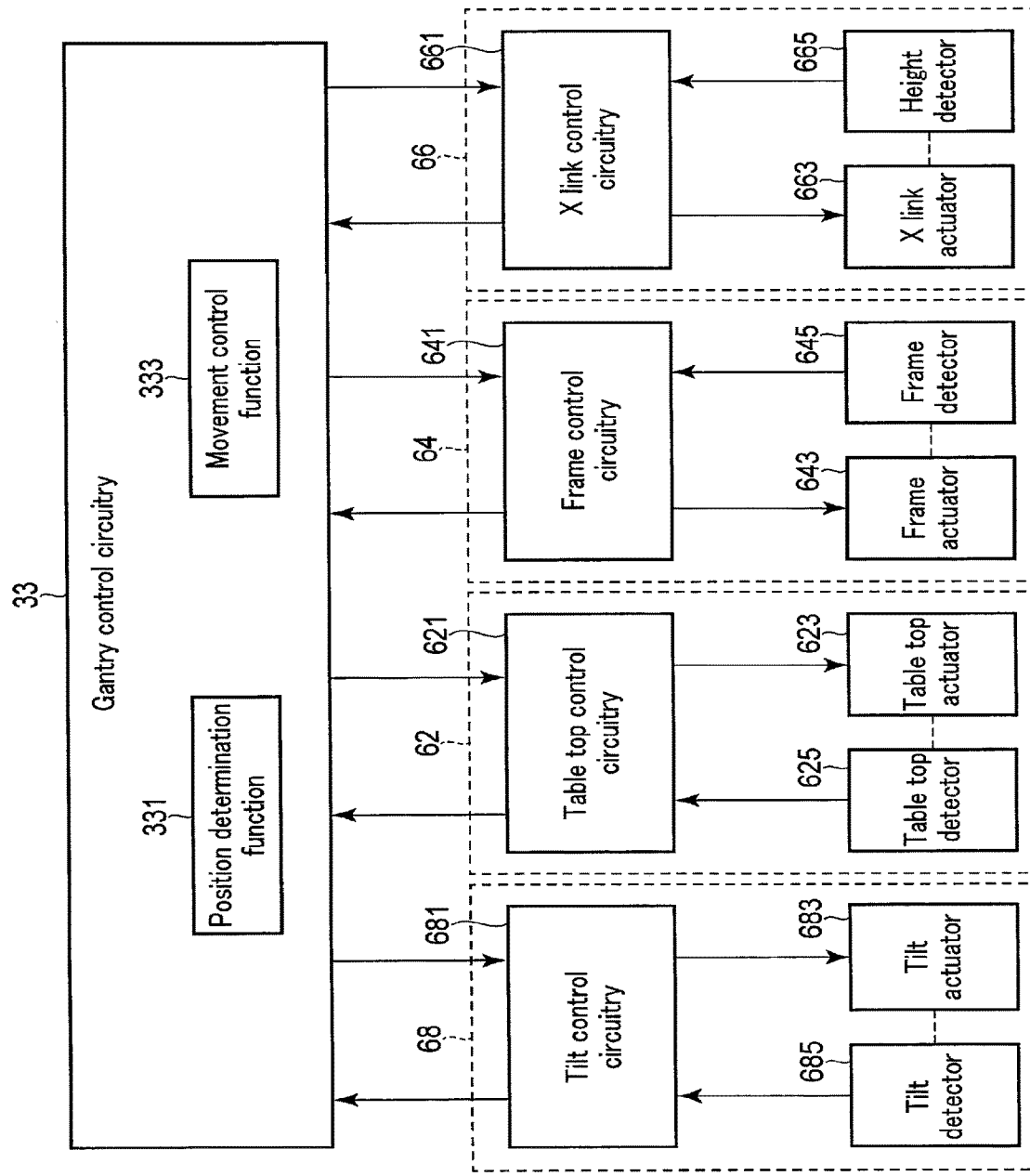
FIG. 6 is a diagram showing a configuration example of a gantry/bed driving system and gantry control circuitry according to the present embodiment.

FIG. 6 is a diagram showing a configuration of the gantry/bed driving system 25 and the gantry control circuitry 33 according to the present embodiment. As shown in FIG. 6, the gantry/bed driving system 25 includes a tilt actuation controller 68, the table top actuation controller 62, the frame actuation controller 64, and the X link actuation controller 66.

The tilt actuation controller 68 is provided on the gantry 10. The tilt actuation controller 68 tilts the gantry 10 upon receipt of an operation instruction signal from the gantry control circuitry 33. Specifically, the tilt actuation controller 68 includes tilt control circuitry 681, a tilt actuator 683, and a tilt detector 685. Upon receipt of the operation instruction signal from the gantry control circuitry 33, the tilt control circuitry 681 supplies electric power corresponding to the operation instruction signal to the tilt actuator 683. Specifically, the tilt control circuitry 681 is a servo amplifier including power supply circuitry that generates electric power to be supplied to the tilt actuator 683, and control circuitry that controls the power supply circuitry based on a position signal from the tilt detector 685. The tilt actuator 683 tilts the gantry 10 upon receipt of the electric power from the tilt control circuitry 681. Specifically, the tilt actuator 683 is a motor that generates motive power by rotation of a drive shaft. The tilt detector 685 is a position detector provided on the drive shaft of the tilt actuator 683. The tilt detector 685 is a rotary encoder that outputs a pulse signal (position signal) each time the drive shaft of the tilt actuator 683 rotates a predetermined angle.

The table top actuation controller 62 is mounted on, for example, the upper frame 61. The table top actuation controller 62 slides the table top 51 upon receipt of the operation instruction signal from the gantry control circuitry 33. Specifically, the table top actuation controller 62 includes table top control circuitry 621, a table top actuator 623, and a table top detector 625. Upon receipt of the operation instruction signal from the gantry control circuitry 33, the table top control circuitry 621 supplies electric power corresponding to the operation instruction signal to the table top actuator 623. Specifically, the table top control circuitry 621 is a servo amplifier including power supply circuitry that generates electric power to be supplied to the table top actuator 623, and control circuitry that controls the power supply circuitry based on a position signal from the table top detector 625. The table top actuator 623 is driven upon receipt of the electric power from the table top control circuitry 621 and actuates the upper frame 61 connected to the table top actuator 623, thereby sliding the table top 51. Specifically, the table top actuator 623 is a motor that generates motive power by rotation of a drive shaft. The table top detector 625 is a position detector provided on the drive shaft of the table top actuator 623. The table top detector 625 is a rotary encoder that outputs a pulse signal (position signal) each time the drive shaft of the table top actuator 623 rotates a predetermined angle.

The frame actuation controller 64 is mounted on, for example, the lower frame 63. The frame actuation controller 64 slides the upper frame 61 upon receipt of the operation instruction signal from the gantry control circuitry 33. Specifically, the frame actuation controller 64 includes frame control circuitry 641, a frame actuator 643, and a frame detector 645. Upon receipt of the operation instruction signal from the gantry control circuitry 33, the frame control circuitry 641 supplies electric power corresponding to the operation instruction signal to the frame actuator 643. Specifically, the frame control circuitry 641 is a servo amplifier including power supply circuitry that generates electric power to be supplied to the frame actuator 643, and control circuitry that controls the power supply circuitry based on a position signal from the frame detector 645. The frame actuator 643 is driven upon receipt of the electric power from the frame control circuitry 641 and actuates the lower frame 63 connected to the frame actuator 643, thereby sliding the upper frame 61. Specifically, the frame actuator 643 is a motor that generates motive power by rotation of a drive shaft. The frame detector 645 is a position detector provided on the drive shaft of the frame actuator 643. The frame detector 645 is a rotary encoder that outputs a pulse signal (position signal) each time the drive shaft of the frame actuator 643 rotates a predetermined angle. The X link actuation controller 66 is mounted on, for example, the support base 55. The X link actuation controller 66 actuates the X link 65 upon receipt of the operation instruction signal from the gantry control circuitry 33, and moves the table top 51 and the support frame 53 up and down. Specifically, the X link actuation controller 66 includes X link control circuitry 661, an X link actuator 663, and a height detector 665. Upon receipt of the operation instruction signal from the gantry control circuitry 33, the X link control circuitry 661 supplies electric power corresponding to the operation instruction signal to the X link actuator 663. Specifically, the X link control circuitry 661 is a servo amplifier including power supply circuitry that generates electric power to be supplied to the X link actuator 663, and control circuitry that controls the power supply circuitry based on a position signal from the height detector 665. The X link actuator 663 is driven upon receipt of the electric power from the X link control circuitry 661 and actuates the X link 65 connected to the X link actuator 663, thereby moving the table top 51 and the support frame 53 up and down. Specifically, the X link actuator 663 is a motor that generates motive power by rotation of a drive shaft. The lead screw 76 is rotated around the shaft center by rotation of the drive shaft, and the X link 65 is pushed and pulled by the nut 78 in cooperation with the rotation of the lead screw 76. As a result, the table top 51 and the support frame 53 are moved up and down. The height detector 665 is a position detector provided on the drive shaft of the X link actuator 663. The height detector 665 is a rotary encoder that outputs a pulse signal (position signal) each time the drive shaft of the X link actuator 663 rotates a predetermined angle.

The gantry control circuitry 33 controls the gantry/bed driving system 25 based on a user's instruction via the input circuitry 31, or a position signal or the like from the tilt detector 685, the table top detector 625, the frame detector 645, and the height detector 665. The gantry control circuitry 33 of this embodiment carries out an operation to correct a displacement in the Z direction of the support frame 53 involved in an upward or downward movement of the table top 51 and the support frame 53 by the X link 65 (hereinafter referred to as a displacement correcting operation). The displacement correcting operation includes an operation to correct protrusion of the support frame 53 toward the gantry 10 involved in the upward movement of the table top 51 and the support frame 53, and an operation to correct a retreat of the support frame 53 from the gantry 10 involved in the downward movement of the table top 51 and the support frame 53. The gantry control circuitry 33 specifically executes a position determination function 331 and a movement control function 333.

In the position determination function 331, the gantry control circuitry 33 determines whether or not the support frame 53 reaches a predetermined position based on position signals from the tilt detector 685, the table top detector 625, the frame detector 645, and the height detector 665. The predetermined position corresponds to a transition point between operation modes. The predetermined position may be defined in any of the X direction (left-right direction), the Y direction (up-down direction), and the Z direction (forward-backward direction). Details of the operation modes will be described later.

In the movement control function 333, the gantry control circuitry 33 individually or synchronously controls the table top actuation controller 62, the frame actuation controller 64, and the X link actuation controller 66, and individually or synchronously moves the table top 51, the support frame 53, and the X link 65. The gantry control circuitry 33 controls the tilt actuation controller 68 and tilts the gantry 10. The gantry control circuitry 33 according to the embodiment switches between operation modes in accordance with a position of the support frame 53. The operation modes of this embodiment include a single operation mode, an acceleration operation mode, and a displacement correction operation mode.

In the single operation mode, the gantry control circuitry 33 individually controls the table top control circuitry 621, the frame control circuitry 641, and the X link control circuitry 661, to individually move the table top 51, the upper frame 61, and the lower frame 63. For example, the gantry control circuitry 33 controls the frame control circuitry 641 to slide the upper frame 61 in the +Z direction or −Z direction. The gantry control circuitry 33 controls the X link control circuitry 661 to move the lower frame 63 up or down by the X link 65.

In the acceleration operation mode, the gantry control circuitry 33 synchronously controls the frame control circuitry 641 and the X link control circuitry 661 to slide the upper frame 61 in the +Z direction in parallel with the protrusion of the lower frame 63 in the +Z direction in accordance with move-up of the lower frame 63. Furthermore, the gantry control circuitry 33 synchronously controls the frame control circuitry 641 and the X link control circuitry 661 to slide the upper frame 61 in the −Z direction in parallel with the retreat of the lower frame 63 in the −Z direction in accordance with move-down of the lower frame 63.

In the displacement correction operation mode, as described above, the gantry control circuitry 33 controls the X link control circuitry 661 and the frame control circuitry 641 to correct the displacement of the upper frame 61 in the Z direction in accordance with move-up and move-down of the lower frame 63 by means of the X link 65. Specifically, when the lower frame 63 is moved up, the gantry control circuitry 33 offsets an approach (protrusion) of the upper frame 61 toward the gantry 10 in accordance with the move-up of the lower frame 63 by a retreat (slide in the −Z direction) of the upper frame 61 away from the gantry 10 to fix the position in the Z direction of the upper frame 61 relative to the gantry 10. When the lower frame 63 is moved down, the gantry control circuitry 33 offsets a retreat of the upper frame 61 from the gantry 10 in accordance with the move-down of the lower frame 63 by an approach (slide in the +Z direction) of the upper frame 61 toward the gantry 10 to fix the position in the Z direction of the upper frame 61 relative to the gantry 10.

Figure 7:
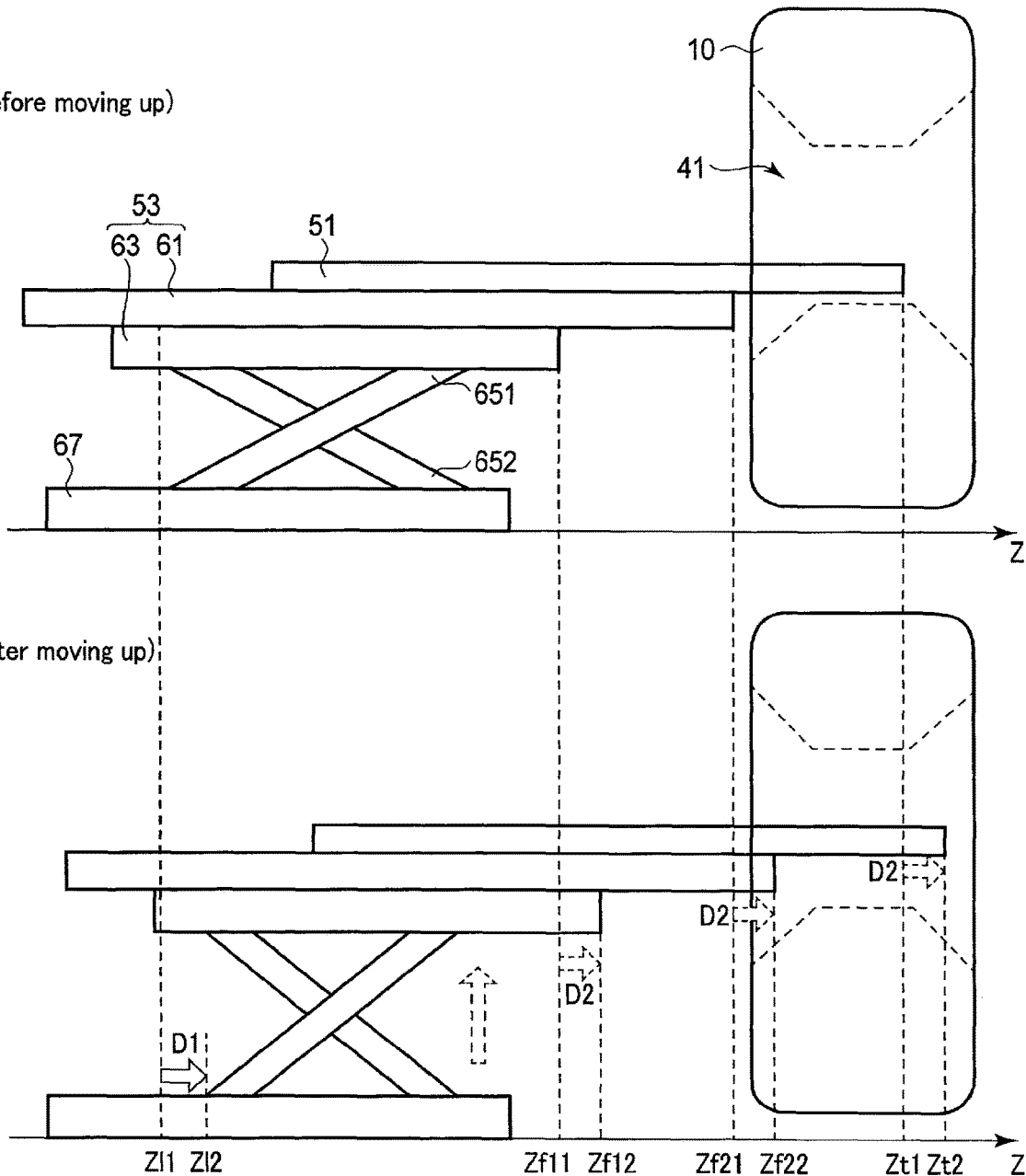
FIG. 7 is a diagram showing a positional relationship between the bed and the gantry before moving up and after moving up, not involving protrusion correction according to the present embodiment.

A displacement correction operation during moving up of the lower frame 63 (hereinafter referred to as a protrusion correction operation) will be explained while comparing FIG. 7 and FIG. 8. FIG. 7 is a diagram showing a positional relationship between the bed 23 and the gantry 10 before move-up and after move-up, not involving a protrusion correction.

It is assumed that the table top 51 is inserted into the bore 41, and the upper frame 61 of the support frame 53 is located just before the front surface of the gantry 10, as shown in an upper half of FIG. 7 (before the move-up). In this state, the end of the movable link 651 of the X link 65 on the base 67 is located at a Z direction position Z11, the end of the lower frame 63 on the side of the gantry 10 is located at a Z direction position Zf11, the end of the upper frame 61 on the side of the gantry 10 is located at a Z direction position Zf21, and the end of the table top 51 on the side of the gantry 10 is located at a Z direction position Zt1.

As shown in a lower half of FIG. 7 (after the move-up), the gantry control circuitry 33 carries out a move-up operation not involving a protrusion correction at a predetermined timing. Specifically, the gantry control circuitry 33 issues an operation instruction for the move-up operation to the X link actuation controller 66, and the X link actuation controller 66 pushes the X link 65 in the +Z direction, thereby moving up the lower frame 63. The upper frame 61 and the table top 51 supported by the lower frame 63 are also moved up. In the case of a move-up operation not involving a protrusion correction, while the X link actuation controller 66 is moving up the lower frame 63, the gantry control circuitry 33 does not issue an operation instruction to the table top actuation controller 62 and the frame actuation controller 64. Therefore, the lower frame 63 protrudes in the +Z direction while moving up.

After moving up, the end of the movable link 651 on the base 67 is located at a Z direction position Z12, the end of the lower frame 63 on the side of the gantry 10 is located at a Z direction position Zf12, the end of the upper frame 61 on the side of the gantry 10 is located at a Z direction position Zf22, and the end of the table top 51 on the side of the gantry 10 is located at a Z direction position Zt2. The amount of movement D1 in the Z direction of the end of the movable link 651 from before to after the move-up of the support frame 53 is defined by a distance from the Z direction position Z11 to the Z direction position Z12. The amount of movement D2 in the Z direction of the end of the lower frame 63 is defined by a distance from the Z direction position Zf11 to the Z direction position Zf12. Since the upper frame 61 and the table top 51 are not moved from before to after the move-up, the amount of movement in the Z direction of the end of the upper frame 61 and the amount of movement in the Z direction of the table top 51 are equal to D2.

The lower frame 63, the X link 65, and the base 67 are arranged so that the direction in which the nut 78 pushes the movable link 651 is almost the same as the direction in which the lower frame 63 protrudes in accordance with the push. Since the lower frame connected to the movable link 651 protrudes due to the push of the movable link 651, the amount of movement D1 of the end of the movable link 651 is almost the same as the amount of movement D2 of the end of the lower frame 63. In this case, since the lower frame 63 protrudes by the amount of movement D2, the upper frame 61 and the table top 51 also protrude by the amount of movement D2.

FIG. 8 is a diagram showing a positional relationship between the bed 23 and the gantry 10 before move-up and after move-up, involving a protrusion correction. As shown in FIG. 8, to correct the protrusion in the Z direction position of the upper frame 61 and the table top 51 after the move-up, the protrusion correction operation is carried out by the gantry control circuitry 33.

The arrangement of the bed 23 and the gantry 10 shown in an upper half of FIG. 8 (before the move-up) is the same as that shown in the upper half of FIG. 7. The gantry control circuitry 33 carries out a move-up operation involving the protrusion correction at a predetermined timing. Specifically, the gantry control circuitry 33 issues an operation instruction for the move-up operation to the X link actuation controller 66, and the X link actuation controller 66 pushes the X link 65 in the +Z direction, thereby moving up the lower frame 63. The upper frame 61 and the table top 51 supported by the lower frame 63 are also moved up. In the case of a move-up operation involving the protrusion correction, while the X link actuation controller 66 is moving up the lower frame 63, the gantry control circuitry 33 issues an operation instruction for the protrusion correction to the frame actuation controller 64. The frame actuation controller 64 offsets a protrusion of the upper frame 61 toward the gantry 10 in accordance with the move-up of the lower frame 63 by a retreat of the upper frame 61 from the gantry 10 to fix an absolute position of the upper frame 61 in the Z direction, so that the upper frame 61 does not move relative to the gantry 10 after the move-up. Specifically, the frame actuation controller 64 moves the upper frame 61 relative to the lower frame 63 by the amount of movement D2, which is the same as the amount of movement D1 of the movable link 651, in the −Z direction opposite to the direction in which the lower frame 63 protrudes.

Due to the protrusion correction operation, the Z direction position Zf22 of the end of the upper frame 61 on the side of the gantry 10 after the move-up approximately coincides with the Z direction position Zf21 before the move-up, and the Z direction position Zt2 of the table top 51 after the move-up is approximately coincides with the Z direction position Zt1 before the move-up. Thus, the table top 51 and the upper frame 61 can be moved up while the absolute positions thereof in the Z direction are fixed.

To accurately correct the protrusion of the lower frame 63, the gantry control circuitry 33 of the present embodiment moves the lower frame 63 based on operation information of the drive shaft of the X link actuation controller 66.

FIG. 9 is a schematic diagram showing flows of operation instruction signals among the gantry control circuitry 33, the X link actuation controller 66, and the frame actuation controller 64 in the protrusion correction operation according to the present embodiment. As shown in FIG. 9, the gantry control circuitry 33 supplies an operation instruction signal PSig relating to a move-up instruction to the X link control circuitry 661. Specifically, during a period when a move-up instruction button of the input circuitry 31 is depressed, the gantry control circuitry 33 supplies a pulse signal series to the X link control circuitry 661 as the operation instruction signal PSig.

The X link control circuitry 661 that receives the operation instruction signal PSig supplies to the X link actuator 663 an operation instruction signal PSig which is the same as the supplied operation instruction signal PSig. The X link actuator 663 that receives the operation instruction signal PSig rotates the drive shaft in accordance with the operation instruction signal PSig, and generates motive power to push the movable link 651 of the X link 65. As a result, the movable link 651 approaches the fixed link 652, and the lower frame 63 moves up.

At this time, the height detector 665 feeds back a feedback signal FB1Sig representing the amount of movement of the movable link 651 to the X link control circuitry 661. Each time the drive shaft of the X link actuator 663 rotates a predetermined angle upon receipt of the operation instruction signal PSig, the feedback signal FB1Sig is immediately output from the height detector 665. Thus, more specifically, the feedback signal FB1Sig represents the amount of movement of the drive shaft of the X link actuator 663. Strictly, the amount of movement corresponds to the amount of rotation of the drive shaft.

The X link control circuitry 661 that receives the feedback signal FB1Sig from the height detector 665 immediately feeds back the feedback signal FB1Sig to the gantry control circuitry 33. The gantry control circuitry 33 that receives the feedback signal FB1Sig from the X link control circuitry 661 immediately supplies the feedback signal FB1Sig to the frame control circuitry 641 as an operation instruction signal relating to a slide instruction in the −Z direction. In other words, the feedback signal FB1Sig output from the height detector 665 is immediately supplied to the frame control circuitry 641 via the X link control circuitry 661 and the gantry control circuitry 33.

The frame control circuitry 641 that receives the operation instruction signal FB1Sig supplies to the frame actuator 643 an operation instruction signal FB1Sig which is the same as the supplied operation instruction signal FB1Sig. The frame actuator 643 that receives the operation instruction signal FB1Sig rotates the drive shaft in accordance with the operation instruction signal FB1Sig, and generates motive power to slide the upper frame 61. As a result, the lower frame 63 slides the upper frame 61 in the −Z direction.

At this time, the frame detector 645 feeds back a feedback signal FB2Sig representing the amount of movement of the upper frame 61 to the frame control circuitry 641. The frame control circuitry 641 feeds back the feedback signal FB2Sig to the gantry control circuitry 33.

This is the end of the explanation of the flows of operation instruction signals among the gantry control circuitry 33, the X link actuation controller 66, and the frame actuation controller 64 in the protrusion correction operation. As described above, the gantry control circuitry 33 of the present embodiment collects the feedback signal FB1Sig representing the amount of movement of the drive shaft of the X link actuator 663 as operation information from the X link control circuitry 661. To move the drive shaft of the frame actuator 643 by the amount of movement that approximately coincides with the amount of movement of the drive shaft of the X link actuator 663, the gantry control circuitry 33 supplies the feedback signal FB1Sig to the frame control circuitry 641.

For example, as a method other than the present embodiment, there may be a case in which the amount of move-up of the lower frame 63 is converted to a position detection signal by a rotary encoder, and an operation instruction signal to slide the upper frame 61 in the −Z direction is generated by utilizing the position detection signal. In this case, since the direction of move-up of the lower frame 63 (+Y direction) is not coaxial with the direction of slide of the upper frame 61 (−Z direction), the amount of move-up of the lower frame 63 needs to be converted to the amount of slide of the upper frame 61 based on the position detection signal from the rotary encoder. Therefore, an accurate protrusion correction cannot be performed.

In contrast, according to the present embodiment, as described above, since the X link 65 is employed as a system for moving up the lower frame 63, the move-up of the lower frame 63 is implemented by the push of the movable link 651 in the +Z direction. With this mechanism, the direction of movement of the movable link 651 (+Z direction) and the direction of slide of the protrusion correction of the upper frame 61 (−Z direction) are coaxial (Z direction); therefore, the amount of movement D1 of the movable link 651 and the amount of movement D2 of the upper frame 61 are strictly the same. Thus, it is only necessary to move the upper frame 61 by the amount of movement D2 which is the same as the amount of movement D1 of the movable link 651, and the feedback signal from the height detector 665 can be directly used as the operation instruction signal. Therefore, according to the present embodiment, more accurate protrusion correction as compared to the conventional art can be carried out. Furthermore, a process of converting a position detection signal to an amount of movement of the upper frame 61 is not necessary. Therefore, in the present embodiment, quick response properties relating to the slide of the upper frame 61 in cooperation with the move-up of the lower frame 63 can be improved as compared to the conventional art.

Although FIG. 9 shows flows of operation instruction signals in the case of moving up the lower frame 63, the feedback may be executed in the same manner also in the case of moving down the lower frame 63.

Next, an example of an operation relating to positioning of the table top 51 by the gantry control circuitry 33 according to the present embodiment will be explained. The gantry control circuitry 33 of the embodiment switches between operation modes in accordance with a position of the bed 23, so that the table top 51 can be brought to an X-ray path at the shortest distance.

Figure 10:
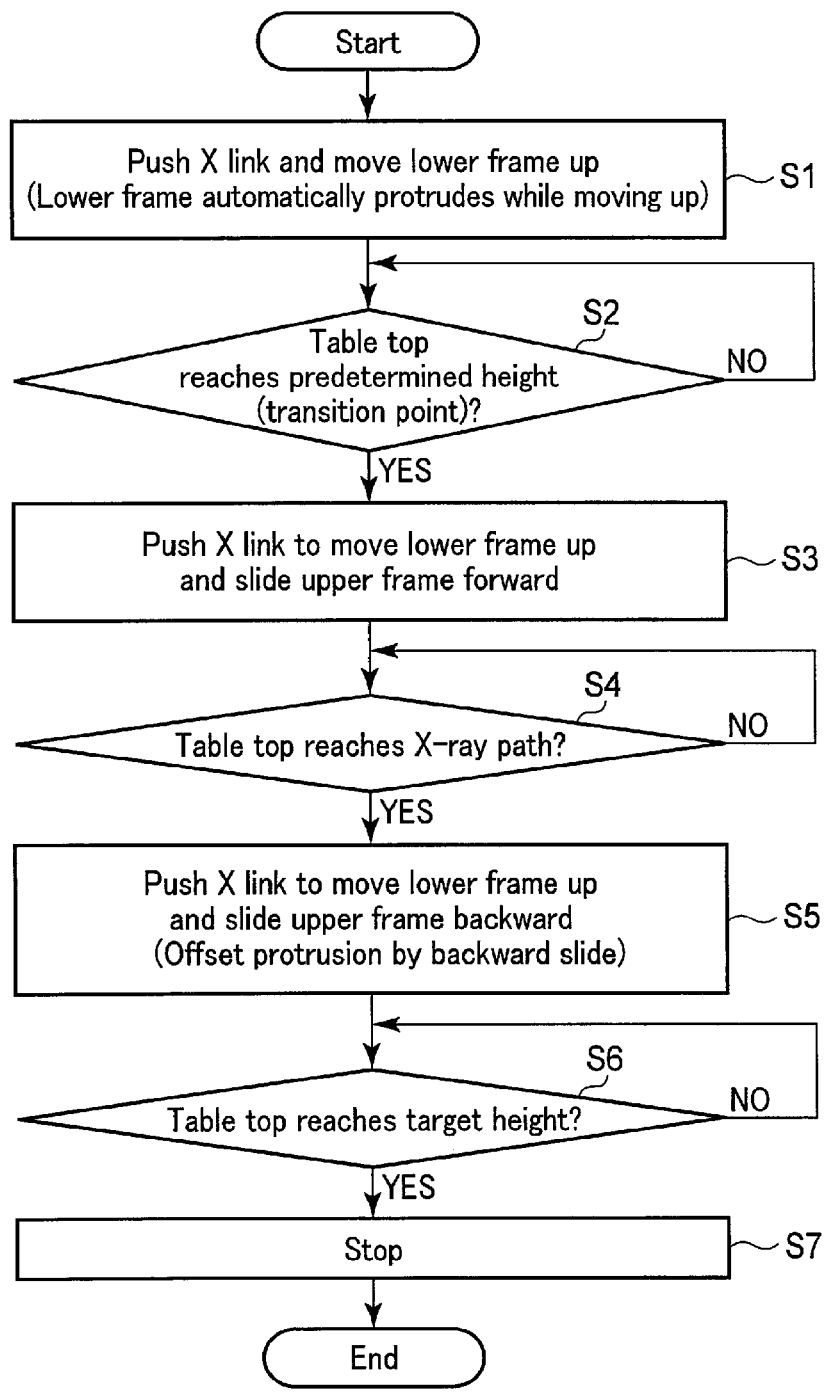
FIG. 10 is a flowchart showing a typical flow of an example of an operation relating to positioning by the gantry control circuitry according to the present embodiment.

FIG. 10 is a flowchart showing a typical flow of an example of an operation relating to positioning by the gantry control circuitry 33. FIG. 11 is a diagram showing a movement path of the table top 51 in the example of the operation shown in FIG. 10. The vertical axis in FIG. 11 is defined as a Y direction position, and the horizontal axis is defined as a Z direction position.

At the start time in FIG. 10, the table top 51 is assumed to be located at an initial position P1. It is assumed that the Y direction position of the initial position P1 is set to be the lower limit of the bed, and the Z direction position is set to be the maximum retreat position. The lower limit of the bed is the lower limit of the table top 51 in the case where the table top 51 is located outside the bore 41. The maximum retreat position is a position where the table top 51 is farthest from the gantry 10 as structurally possible. At the time of start in FIG. 10, the operation mode of the gantry control circuitry 33 is assumed to be the single operation mode.

First, the user depresses the move-up instruction button to instruct to move up the table top 51 via the input circuitry 31 to position the table top 51, so that a reference point of the table top 51 coincides with a target position P4. The reference point of the table top 51 may be set at any position in the table top 51. The Y direction position of the target position P4 is set between a lower limit in the bore and an upper limit in the bore. The lower limit in the bore is the lower limit of the table top 51 in the case where the table top 51 is located within the bore 41. The upper limit in the bore is the upper limit of the table top 51 in the case where the table top 51 is located within the bore 41. The Z direction position of the target position P4 is set on an X-ray path connecting the X-ray tube 13 and the X-ray detector 15. A target position of the upper frame 61 is also set in accordance with the target position of the table top 51. The target position of the upper frame 61 is set so that the end of the upper frame 61 on the side of the gantry 10 is located just before the front surface of the gantry 10. Thus, since a large part of the table top 51 is supported by the upper frame 61, the bending and vibration of the table top 51 within the bore 41 can be reduced. Accordingly, an image of high definition can be reconstructed.

The move-up instruction button is, for example, a deadman switch. During a period when the move-up instruction button is depressed, the gantry control circuitry 33 performs processing of the following steps S1 to S7. When the move-up instruction button is released, the gantry control circuitry 33 suspends the processing. When the move-up instruction button is depressed again, the gantry control circuitry 33 resumes the suspended processing.

While the user is depressing the button, the gantry control circuitry 33 controls the X link control circuitry 661 to move the lower frame 63 up by pushing the X link 65 (step S1). As indicated by a route R1 (a bold line) in FIG. 11, the lower frame 63 automatically protrudes in the +Z direction as it is moved up by the X link 65. As the lower frame 63 protrudes, the table top 51 and the support frame 53 supported by the lower frame 63 also automatically protrude in the +Z direction.

While the lower frame 63 is moving up, the gantry control circuitry 33 executes the position determination function 331 (step S2). In step S2, the gantry control circuitry 33 repeatedly determines whether the table top 51 reaches a predetermined height (transition point) P2. The transition point P2 is defined to be a height where the single operation mode is switched to the acceleration operation mode.

If it is determined that the table top 51 reaches the transition point P2 (step S2: YES), the gantry control circuitry 33 switches the operation mode from the single operation mode to the acceleration operation mode (step S3). In step S3, the gantry control circuitry 33 synchronously controls the frame control circuitry 641 and the X link control circuitry 661 to push the X link 65 and move the lower frame 63 up, as indicated by the route R1 shown in FIG. 11, and also to slide the upper frame 61 in the +Z direction (forward).

In the acceleration operation mode, the gantry control circuitry 33 executes the position determination function 331 (step S4). In step S4, the gantry control circuitry 33 repeatedly determines whether the table top 51 reaches an X-ray path, more specifically, an intermediate point P3. The Y direction position of the intermediate point P3 is set to the lower limit in the bore, and the Z direction position is set on the X-ray path in the bore.

As shown in FIG. 11, the table top 51 can be moved from the transition point P2 to the intermediate point P3 only in the single operation mode without using the acceleration operation mode. In this case, for example, as indicated by a route R2 (a thin line in FIG. 11), the lower frame 63 is continuously moved up in the single operation mode even after passing through the transition point P2. After the lower frame 63 reaches the lower limit in the bore, the move-up of the lower frame 63 is stopped and the upper frame 61 is slid in the +Z direction, as indicated by a route R3 (a chain line in FIG. 11). However, as in the case of the present embodiment in which the single operation mode is switched to the acceleration operation mode at the transition point P2, the upper frame 61 is actively slid in the +Z direction along with the protrusion of the lower frame 63 in the +Z direction in accordance with the move-up of the lower frame 63 from the transition point P2 to the intermediate point P3, so that the table top 51 passes a shortest route R1. As a result, the distance from the transition point P2 to the intermediate point P3 can be shortened, and the table top 51 can reach the intermediate point P3 in a shorter time.

If it is determined that the table top 51 reaches the X-ray path (step S4: YES), the gantry control circuitry 33 switches the operation mode from the acceleration operation mode to the protrusion correction operation mode (step S5). In step S5, the gantry control circuitry 33 controls the frame control circuitry 641 and the X link control circuitry 661 to push the X link 65 and move the lower frame 63 up, and also to slide the upper frame 61 in the −Z direction (backward). Due to the protrusion correction as described above, the table top 51 and the upper frame 61 can be moved up, while the Z direction positions of the table top 51 and the upper frame 61 are fixed.

In the protrusion correction operation mode, the gantry control circuitry 33 executes the position determination function 331 (step S6). In step S6, the gantry control circuitry 33 repeatedly determines whether or not the table top 51 reaches a target height, more specifically, an target position P4. If it is determined that the table top 51 reaches the target height, the gantry control circuitry 33 stops controlling the frame control circuitry 641 and the X link control circuitry 661. Thus, the positioning of the table top 51 and the support frame 53 is completed.

This is the end of the explanation of an example of an operation relating to positioning of the table top 51 and the support frame 53 by the gantry control circuitry 33 according to the present embodiment.

As described above, the gantry control circuitry 33 of the present embodiment can move the table top 51 and the support frame 53 to the target position P4 through the shortest route R1 by switching among the single operation mode, the acceleration operation mode, and the protrusion correction operation mode in accordance with the positions of the table top 51 and the support frame 53. Furthermore, while the lower frame 63 is moving up, the gantry control circuitry 33 slides the upper frame in the direction opposite to the protrusion of the lower frame 63 in the same amount, so that the displacement of the table top 51 and the support frame 53 in the Z direction can be prevented. As a result, the efficiency of positioning of the table top 51 and the support frame 53 can be improved.

The movement from the initial position P1 to the target position P4 has been described above as an example of operation. However, the gantry control circuitry 33 of the present embodiment can move the table top 51 from the target position P4 to the initial position P1 via the same shortest route R1 in a process inverse to the steps from the initial position P1 to the target position P4. As a result, the time of movement from the target position P4 to the initial position P1 can be reduced, and accordingly the throughput of CT examination can be improved.

Furthermore, in the example of operation described above, whether the position of the table top 51 reaches the transition point P2, the intermediate point P3, or the target position P4 is determined in real time. However, the embodiment is not limited to the description. For example, the shortest route R1 that connects the initial position P1 and the target position P4 and that does not cause the table top 51 and the gantry 10 to interfere with each other may be determined by calculation in advance. In this case, an operation sequence is determined for each of the table top control circuitry 621, the frame control circuitry 641, and the X link control circuitry 661 to make the table top 51 pass through the shortest route R1. The gantry control circuitry 33 controls the table top control circuitry 621, the frame control circuitry 641, and the X link control circuitry 661 based on the operation sequences, so that the table top 51 passes through the shortest route R1.

In the example of the operation described above, the gantry control circuitry 33 slides the upper frame 61 in cooperation with the move-up and move-down of the lower frame 63 by the X link 65. More specifically, the X link 65 is actuated when a pulse signal is input to the X link control circuitry 661, and each time the drive shaft of the X link 65 rotates a predetermined angle, a pulse signal as a feedback signal is immediately output. When the feedback signal is input to the frame control circuitry 641, the lower frame 63 is actuated and the upper frame 61 is slid. In other words, the move-up or move-down of the lower frame 63 by the X link control circuitry 661 and the slide of the upper frame 61 by the frame control circuitry 641 are described as being alternately carried out. However, the embodiment is not limited to the description. For example, the gantry control circuitry 33 may carry out the slide of the upper frame 61 by the frame control circuitry 641 after the lower frame 63 has been moved to a predetermined height by the X link control circuitry 661.

Furthermore, in the above example of operation, a tilt angle of the gantry 10 may be set to 0 degrees or any other angle greater than 0 degrees. The Z direction position and the Y direction position of the transition point P2 is determined in accordance with the tilt angle so that the table top 51 and the support frame 53 do not interfere with the gantry 10.

Furthermore, in the above example of operation, the target position of the upper frame 61 is described as being just before the front surface of the gantry 10. However, the embodiment is not limited to the description. For example, to obtain an image of high definition, the target position of the upper frame 61 may be set as close as possible to the gantry 10, whereas to perform a tilt operation of the gantry 10 preferentially, the target position of the upper frame 61 may be set away from the gantry 10.

(Overview)

As described above, the X-ray computed tomography apparatus of the embodiment includes at least the gantry 10, the upper frame 61, the lower frame 63, the support base 55, and the gantry control circuitry 33. The gantry 10 is equipped with the X-ray tube 13 and the X-ray detector 15. The upper frame 61 supports the table top 51 on which the subject O is laid. The lower frame 63 supports the upper frame 61 so that the upper frame 61 is slidable in the Z direction. The support base 55 is equipped with the X link 65 that supports the lower frame 63, so that the lower frame 63 is movable in the Y direction. The gantry control circuitry 33 moves the upper frame 61 based on operation information of the drive shaft to actuate the X link 65 to correct the Z direction position of the upper frame 61 that changes as the lower frame 63 moves in the Y direction.

With the configuration described above, when the lower frame 63 is moved up and down by the X link 65, the Z direction position of the upper frame 61 can be fixed. Therefore, repositioning of the table top 51 after the move-up or move-down is unnecessary. Furthermore, since the X link 65 moves in the same direction as the direction of movement of the upper frame 61, thereby moving the lower frame 63 up and down, the gantry control circuitry 33 according to the embodiment utilizes operation information on the drive shaft of the X link 65, so that the amount of movement of the upper frame 61 in the forward-backward direction in accordance with the move-up and move-down of the lower frame 63 can be accurately corrected.

Thus, according to the embodiment, in the medical image diagnosis apparatus and the bed apparatus of the type in which the table top and the support frame move forward and backward while moving up and down, the efficiency of positioning of the table top and the support frame can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimded is:

1. A medical diagnostic apparatus comprising:
    a gantry;
    a first frame that supports a table top, on which a subject is to be laid, so that the table top is movable in a longitudinal direction of the table top toward the gantry;
    a second frame that supports the first frame, so that the first frame is movable in the longitudinal direction;
    a support base equipped with an X link that supports the second frame, so that the second frame is movable in a vertical direction perpendicular to a floor surface; and
    movement control circuitry that moves the first frame in the longitudinal direction based on operation information of a first shaft of the support base to correct a change in position of the first frame in the longitudinal direction in accordance with movement of the second frame in the vertical direction.

2. The medical diagnostic apparatus according to claim 1, wherein when the second frame is moved up, the movement control circuitry offsets an approach of the first frame toward the gantry in accordance with move-up of the second frame by a retreat of the first frame away from the gantry to fix a position of the first frame relative to the gantry.

3. The medical diagnostic apparatus according to claim 1, wherein when the second frame is moved down, the movement control circuitry offsets a retreat of the first frame from the gantry in accordance with move-down of the second frame by an approach of the first frame toward the gantry to fix a position of the second frame relative to the gantry.

4. The medical diagnostic apparatus according to claim 1,
    wherein the support base comprises the X link, a base that supports the X link, an X link actuator including the first shaft to actuate the X link, and X link control circuitry that controls the X link actuator;
    wherein the second frame comprises a slide mechanism that supports the first frame so that the first frame is slidable in the longitudinal direction, a slide actuator including a second shaft to actuate the slide mechanism, and slide control circuitry that controls the slide actuator; and
    wherein the movement control circuitry collects a feedback signal representing an amount of movement of the first shaft as the operation information from the X link control circuitry, and supplies the collected feedback signal to the slide control circuitry to move the second shaft by an amount that is approximately same as the amount of movement.

5. The medical diagnostic apparatus according to claim 1,
    wherein the support base comprises the X link, and a base that supports the X link; and
    wherein the X link comprises a pair of links pivotally supported to form an X shape, a first end of a first link of the pair of links is fixed to the base, a second end of the first link is fixed to the second frame, a first end of a second link of the pair of links is slidably supported by the base, and a second end of the second link is slidably supported by the second frame.

6. The medical diagnostic apparatus according to claim 5,
    wherein the support base further comprises an X link actuator that rotates the first shaft to move up or move down the second frame, to push or pull the second link in a horizontal direction that is approximately same as the longitudinal direction; and
    wherein the operation information represents an amount of rotation of the first shaft that defines an amount of movement in the horizontal direction that is approximately same as the longitudinal direction of the table top.

7. The medical diagnostic apparatus according to claim 1, wherein the movement control circuitry alternately carries out movement of the second frame by the support base and movement of the first frame by the second frame.

8. The medical diagnostic apparatus according to claim 1, the movement control circuitry carries out movement of the first frame by the second frame after completion of movement of the second frame by the support base.

9. A medical diagnostic apparatus comprising:

a gantry;

a first frame that supports a table top, on which a subject is to be laid, so that the table top is movable in a longitudinal direction of the table top toward the gantry;

a second frame that supports the first frame, so that the first frame is movable in the longitudinal direction;

a support base equipped with an X link that supports the second frame, so that the second frame is movable in a vertical direction perpendicular to a floor surface, and a base that supports the X link, the X link including a pair of links pivotally supported to form an X shape, a first end of a first link of the pair of links being fixed to the base, a second end of the first link being fixed to the second frame, a first end of a second link of the pair of links being slidably supported by the base, and a second end of the second link being slidably supported by the second frame; and movement control circuitry that moves the second frame in the vertical direction without changing a predetermined position of the second frame in the longitudinal direction.

10. A bed apparatus comprising:

a first frame that supports a table top, on which a subject is to be laid, so that the table top is movable in a longitudinal direction of the table top;

a second frame that supports the first frame, so that the first frame is movable in the longitudinal direction; and a support base equipped with an X link that supports the second frame, so that the second frame is movable in a vertical direction perpendicular to a floor surface, wherein the second frame moves in the longitudinal direction based on operation information of a drive shaft of the support base to correct a change in position of the first frame in the longitudinal direction in accordance with movement of the second frame in the vertical direction.

\* \* \* \* \*